United States Patent [19]

Sisbarro et al.

[11] Patent Number: 6,044,693
[45] Date of Patent: Apr. 4, 2000

[54] METHOD AND APPARATUS FOR UNROLLING PROPHYLACTIC DEVICES

[75] Inventors: Frederick P. Sisbarro, Wayne; William D. Platt, Mount Holly; Glenn W. Thomsen, Cream Ridge, all of N.J.

[73] Assignee: Carter-Wallace, Inc., New York, N.Y.

[21] Appl. No.: 09/190,642

[22] Filed: Nov. 12, 1998

[51] Int. Cl.$^7$ .................................................. B65G 51/02
[52] U.S. Cl. ............................................. 73/41; 406/108
[58] Field of Search .................... 73/40, 41; 29/DIG. 28, 29/DIG. 63; 406/109, 110, 112, 151, 154, 157, 176, 197, 198, 108

[56] References Cited

U.S. PATENT DOCUMENTS

5,846,030 12/1998 Beard et al. .

*Primary Examiner*—Robert Raevis
*Attorney, Agent, or Firm*—Watov & Kipnes, P.C.

[57] ABSTRACT

A plurality of rolled-up prophylactic devices are passed through a plurality of pairs of unroller tubes with a randomizer vessel being coupled between each pair of unroller tubes, the randomizer vessels functioning to randomly reorient a portion of rolled-up ones of the prophylactic devices passing therethrough to move a rolled-up portion of each of the latter to the outside of the associated prophylactic device to facilitate unrolling of the same as it passes from the randomizer vessel into another one of the unroller tubes. A separator tank has an inlet port coupled to an output end of the last occurring unroller tube, for collecting the processed prophylactic devices, and for applying a vacuum to the system for sucking the prophylactic devices through the unroller tubes and randomizer vessels.

26 Claims, 5 Drawing Sheets

METHOD AND APPARATUS FOR UNROLLING PROPHYLACTIC DEVICES

FIELD OF THE INVENTION

The field of the present invention relates generally to methods and apparatus for manufacturing prophylactic devices, and more particularly to methods and apparatus for unrolling prophylactic devices.

BACKGROUND OF THE INVENTION

During the manufacture of prophylactic products, such as condoms, gloves, finger cots, and so forth, such devices or products are typically formed on a mandrel having the shape of the desired product. The mandrel is typically coated with prophylactic material in a liquid state, followed by curing or drying of the material upon the mandrel to form the prophylactic product. After drying or curing the material, the product is often removed from the mandrel by rolling the product up and off the mandrel. Prophylactic products such as condoms require 100% testing to insure that the condom is free of holes that could permit undesirable germs, virus, or other material to escape from or enter into the interior of the condom. Also, prophylactic products, such as surgical gloves require testing after manufacture to insure there are no holes that would permit germs or viruses to pass from the glove interior to the outside, or to pass from outside into the glove interior to the skin of a user's hand or fingers. In order to properly test a prophylactic device for holes, the device may first be fully unrolled to permit standardized testing to be performed, such as electronic testing, and so forth.

The unrolling of a prophylactic device to permit testing of the device can be performed by hand. However, this is very labor intensive, and time consuming. Accordingly, it is desirable to automate the unrolling process for the prophylactic devices.

SUMMARY OF INVENTION

An object of the invention is to provide an improved method and apparatus for unrolling/unsnapping prophylactic devices.

It is a further object of the invention to provide a low cost and highly reliable method and apparatus for automatically insuring the complete unrolling of a large number of prophylactic devices in a manner where a high percentage of the prophylactic devices or products are unrolled in a first pass through the apparatus.

With these and other objects in mind, the present invention provides for sucking a plurality of prophylactic devices or products through elongated tubes having an inside diameter close to the outside diameter of a rolled-up prophylactic device to be unrolled, with the inside walls of the elongated tubes being made so that they do not impart damage to the prophylactic device. Prophylactic devices sucked through a sufficient length of such tubing will be unrolled if as they pass through the tube, the rolled portion of the prophylactic device is on the outside of the device and at the upstream end of tubing. A prophylactic device so oriented will be unrolled by the effect of inflation and the frictional forces imposed upon the prophylactic device by the side walls of the tubing through which it is moving. On a random basis about one-half of the prophylactic devices are so oriented upon entry into the tubing, and will be unrolled in a first pass through the tubing. In the present invention, the exit end of the tubing is connected to an input port located at the bottom of a glass vessel of a desired shape. An output port centrally located at the bottom of the vessel is connected to an input end of a second elongated tubing for transporting the prophylactic devices that are passed through the vessel. The other end of the second tubing can be connected to the input port of another vessel, or directly to a vacuum source. Unrolled ones of the prophylactic devices passing into the vessel will stay unrolled, and move through a portion of the interior volume of the vessel, and then exit from the bottom central exit port into the second elongated tubing for passage to a collection bin, or to another vessel. In using just one vessel, representing a vacuum chamber, the rolled or partially unrolled prophylactic devices passing into the vessel, move through the interior volume of the vessel and tend to be randomly reoriented, whereby many of the rolled or partially unrolled prophylactic devices will exit from the exit port of the vessel with the rolled portion now on the outside, whereby in passing through the second elongated tube the properly oriented rolled-up or partially unrolled prophylactic devices will be unrolled. By cascading a plurality of vacuum vessels in the manner indicated, substantially all of the initially rolled-up prophylactic devices can be automatically unrolled. Typically, the free end of the last elongated tubing through which the prophylactic products flow is connected into the interior of a separator tank, in which the prophylactic devices or product drop to the bottom of the tank for removal therefrom.

BRIEF DESCRIPTION OF THE DRAWINGS

Various embodiments of the present invention are described below with reference to the drawings, in which like items are identified by the same reference designation, wherein.

DETAILED DESCRIPTION OF THE INVENTION

Figure 1:
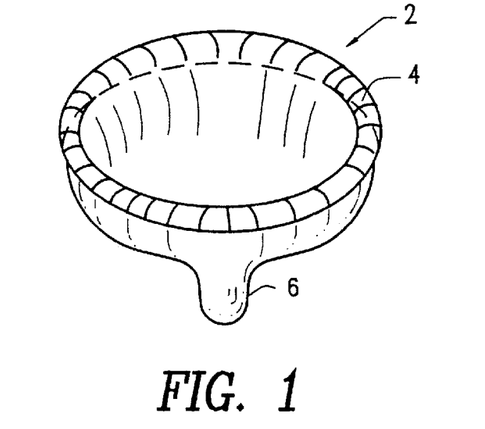
FIG. 1 shows a rolled-up prophylactic device, in this example a condom, with a rolled-up portion or roll on the outside of the device.

As shown in FIG. 1, a rolled-up prophylactic device, in this example a condom 2, has its rolled-up portion 4 positioned on the outside of the condom 2. Note that in this example, the condom 2 is shown to have a reservoir or nipple portion 6 projecting from the center of its closed end.

Figure 2:
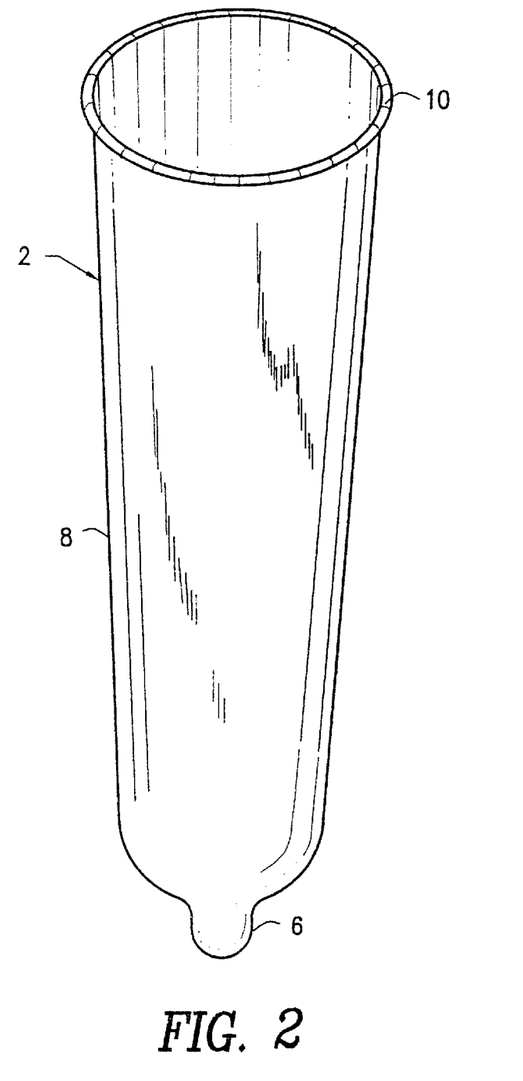
FIG. 2 shows the condom of FIG. 1 in a typically unrolled state preparatory to testing or use.

With the rolled portion 4 on the outside, it is relatively easy to unroll a condom 2 either by grasping the bottom portion and pulling upward on the rolled portion 4, or by frictionally engaging the outer circumference of the ring 4 while inflating the condom in a manner that the roll 4 is allowed to unroll itself. When unrolled, a condom 2 appears as shown in FIG. 2, and has an elongated relatively thin wall tubular portion 8, and a ring 10 about its open end.

Figure 3:
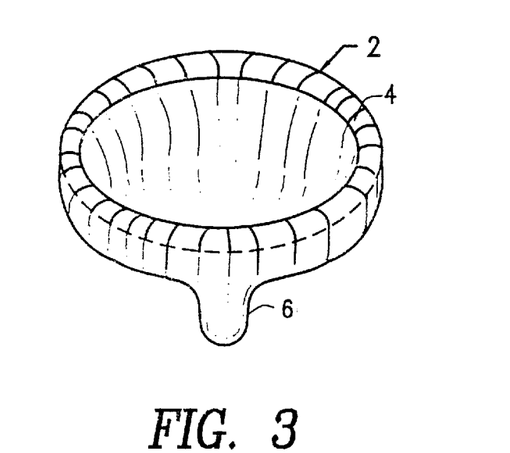
FIG. 3 shows a rolled-up condom with the roll positioned on the inside of the condom.

If for the condom 2 of FIG. 1, the slightly extended portion is pushed back through the rolled-up portion 4, the rolled-up portion 4 will then be positioned on the inside of the condom, as shown in FIG. 3. When a condom 2 is oriented with the rolled-up portion 4 on the inside, it is more difficult to unroll the condom 2, either manually or through some mechanical means.

Figure 4:
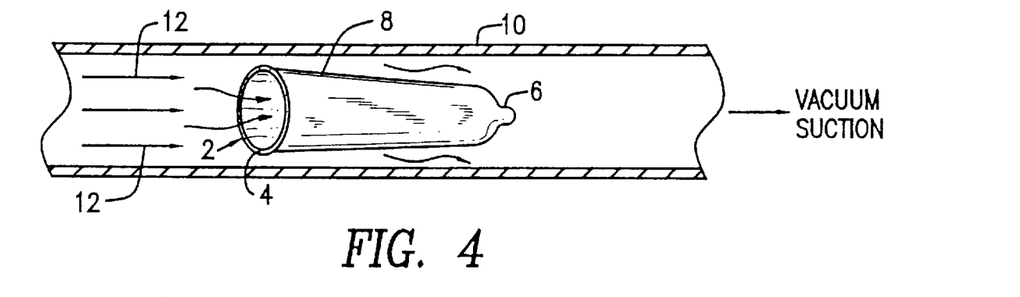
FIG. 4 shows a condom oriented with the roll on the outside being passed through an elongated tubing in an inflated state for unrolling the condom.

In the present invention, as shown in FIG. 4, condoms 2 are unrolled by feeding them into one end of an elongated tube 10, whereby in this example the other end of the tube 10 is connected to a vacuum source. As a result the condoms 2 are sucked down the full length of the tube 10 by the vacuum source sucking the condoms 2 toward the opposite end of the tube 10, and further by air rushing in behind a condom 2 from the feed end of the tube 10, as shown. The direction of movement of condoms 2 and the airflow in the tube 10 are indicated by the arrows 12.

In the preferred embodiment of the invention, the inside diameter of the tubes 10 are made slightly larger than the outside diameter of a rolled-up condoms 2. Also, the interior walls of the tubes 10 are made to provide as low a coefficient of friction as possible and be as non-tacky as practical, to prevent damage to the condoms 2 traveling through the tubes 10. The tubes 10 are typically made from flexible plastic material. However, the tubes 10 can be made from any suitable material. The condoms 2 typically consist of latex or polyurethane material, and as such can be damaged by either rough portions of the interior walls of the tubes 10, or by heat generated in passing through the tubes 10, if the interior walls tend to be sticky or impart excessive frictional forces upon the condoms 2 passing through.

The condoms 2 are fed into the tubes 10 from a supply source in a random manner relative to orientation thereof, whereby at any given time perhaps half of the condoms 2 will enter the tubes with the rolled-up portion on the outside, and half with the rolled-up portion in the inside of the condoms 2 as previously explained. As a result, in passing typical condoms 2 through a tubing 10, preferably of at least six-feet in length, only 40% to 60% of the condoms 2 will be unrolled by the time they exit from the other end of the tube 10. This means that the condoms 2 that pass through the tube 10 must be sorted to retrieve the unrolled ones, and pass them through the tube 10 again. Obviously, this is a time consuming and inefficient way to unroll the condoms 2, for further processing or testing.

Figure 5:
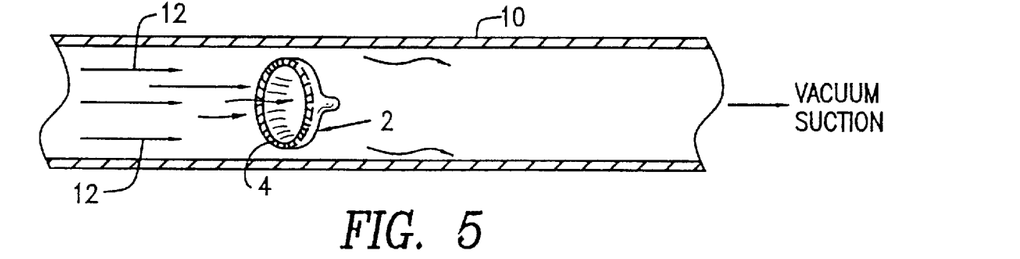
FIG. 5 shows a rolled-up condom with the roll on the inside as the condom is passing through an elongated tubing.

More specifically, as shown in FIG. 4, a condom 2 that enters a tube 10 with its rolled portion 4 on the outside, will be unrolled as shown as it passes through the tube 10 by the action of air rushing in behind the condom 2 inflating it, and causing the rolled portion 4 to unroll as it engages portions of the inside walls of the tube 10. Contrary to this, as shown in FIG. 5, if a condom 2 enters the tube 10 with the rolled-up portion on the inside, it typically will be sucked and pushed through the tube 10 without being fully unrolled, as shown.

Figure 6:
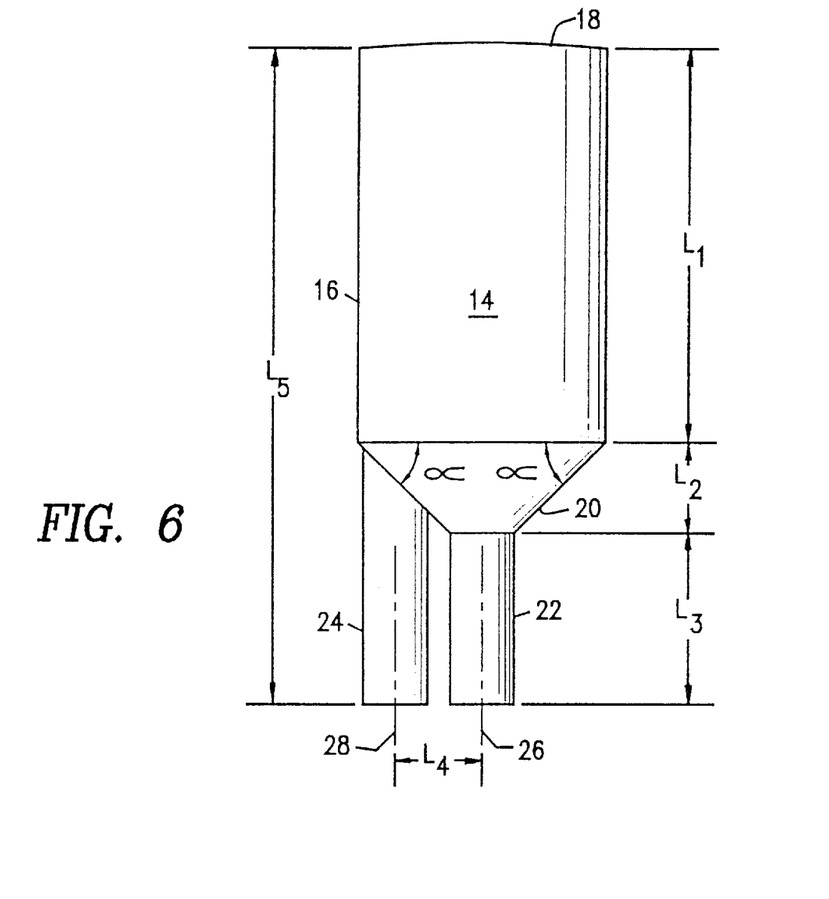
FIG. 6 shows a side elevation view of a vacuum vessel used as a randomizer in one embodiment of the invention.

After much experimentation, the inventors discovered apparatus for permitting almost all of the condoms 2 passed through the unrolling apparatus to be unrolled on a first pass through the apparatus. A key portion of the apparatus is the use of one or more specially designed vessels 14, as shown in FIG. 6. Note that the vessel 14, as shown, is not to scale. As will be explained, the vessel 14 serves as a randomizer for reorienting rolled and partially unrolled condoms 2 received from an unrolling tube 10, and thereafter feeding the reoriented condoms 2 into another length of unrolling tubes 10.

In the preferred embodiment, the vessel 14 consists of a glass cylinder 16, having a rounded or convex closed top 18, a truncated funnel-shaped or truncated cone lower portion 20, a centrally located exit or output tube 22, and input tube 24 located as shown. Clear glass is used, in order to permit an operator to watch the condoms 2 passing through the vessel 14. It is preferred to use glass, not only because of its transparency, but also because it provides for good economics due to the low cost of the glass material, and also facilitates obtaining very smooth interior walls and transitions in the vessel 14. Other materials can be used to provide the vessel 14, including stainless steel, plastic, or any other suitable material. With further reference to the preferred embodiment for a vessel 14, the length $L_1$ is three feet, inside diameter is eight and half inches, and outside diameter is nine inches, whereby the wall thickness is one-quarter inch. For the lower conical or funnel-shaped portion 20, the axial length $L_2$ is two and one-eighth inches, and the angle $\alpha$ is 30°. The length $L_3$ of the exit tube 22 is four and seven-eighths inches. The distance $L_4$ between the longitudinal axis 26 of exit tube 22, and the longitudinal axis 28 of input tube 24 is three and one-eighth inches. The overall length $L_5$ of the vessel 14 is forty-four inches. The outside diameter of each one of the exit tube 22 and input tube 24 is one and three-quarter inches, whereas the inside diameter of these tubes is one and one-half inches, respectively. Accordingly, the wall thickness of the tubes 22 and 24 are one-eighth inch. The dimensions given are preferred for unrolling condoms 2 consisting of polyurethane material.

For condoms 2 of material other than polyurethane, or of certain specific configurations, or for prophylactic products other than condoms, the particulars of the randomizer vessel 14 may preferably be other than those illustrated herein. In other words, the dimensions, entrance and exit tube locations, and vessel geometry tend to be dependent upon the particular prophylactic product being unrolled. To help insure against damage to the prophylactic devices, the entrance and exit edges of tubes 22 and 24 must be rounded and smooth to avoid nicking the prophylactic devices as they enter and exit vessel 14.

Also, in the preferred embodiment for this illustration, a clear plastic coating is used on the exterior walls of the vessel 14 as a safety measure. If a vessel 14 should break, the plastic coating will tend to substantially reduce the chance that glass particles will be strewn about. Note further that the vessel 14 is designed to withstand a continuous vacuum of ten-inches of mercury.

Figure 7:
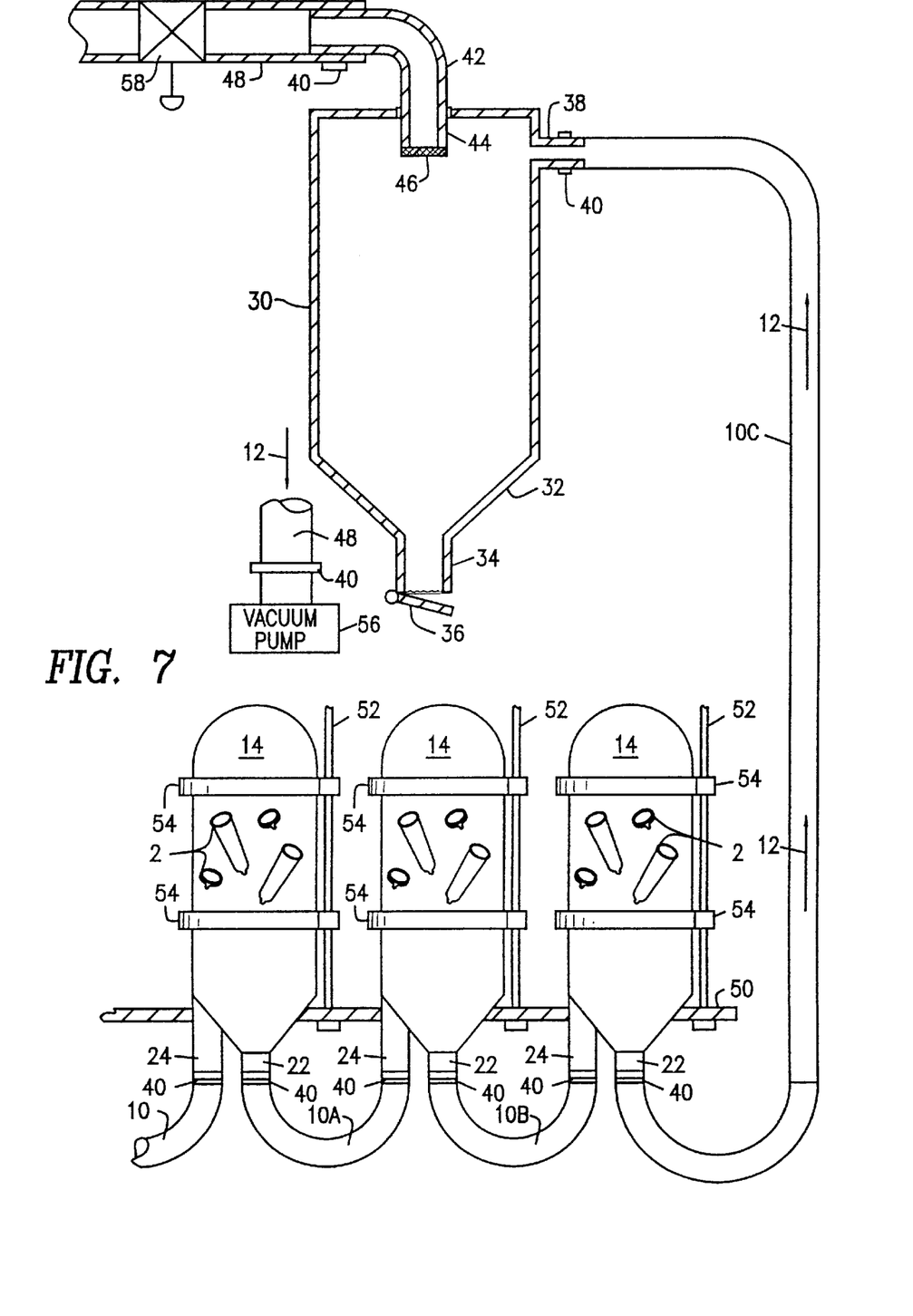
FIG. 7 shows a partial pictorial and partial sectional view of an unrolling system and apparatus for one embodiment of the invention.

In FIG. 7, three randomizer vessels 14 are connected in cascade or series. It was determined by the inventors after experimentation that almost all of the condoms 2 passing through the apparatus can be unrolled through use of three randomizer vessels 14. To substantially guarantee that all of the condoms will be unrolled through the apparatus, more than three randomizer vessels can be used, but it was determined that this was not economically practical due to airflow restrictions in this system. In FIG. 7, a simplified illustration is shown of an engineering prototype built by the inventors. As shown, the input port tube 24 of a first randomizer vessel 14 is connected to the exit end of an unroller tube 10, for receiving condoms 2 therefrom. The exit port tube 22 of the first randomizer vessel 14 is connected via another unroller tube 10A to the input port or tube 24 of a second vessel 14. The exit tube or port 22 of the second vessel 14 is connected via another unroller tube 10B to the input port 24 of a third randomizer vessel 14. The output port 22 of the third randomizer vessel 14 is connected via another unroller tube 10C to a separator tank 30. The separator tank 30 is a fifty-five-gallon drum manufactured by Invincible AirFlow Systems located in Baltic, Ohio, under the model name "Invincible".

The separator tank 30 is typically fabricated from steel material. The tank 30 includes a cone-shaped lower portion 32, a product outlet tube 34 at the bottom of the cone-shaped portion or funnel port 32, with a flapper valve 36 mounted at the exit opening of the product tube 34. A product input port 38 is located near the top of the tank for connection to an end of the unroller tube 10C. Note that the plastic tubing 10, 10A, 10B, and 10C are secured to the aforesaid inlet and outlet ports through use of appropriate tubing clamps 40, as would be known to one of skill in the art. The top of the separator tank 30 is closed off except for a central vacuum port formed by an elbow tube 42 that protrudes at one end 44 into the separator tank 30, as shown. Screening material 46 covers the opening at the end of the interior portion 44 of elbow 42. The other end of the elbow 42 is connected to a six inch flexible plastic tubing 48 secured by a tube clamp 40 to the open end of the elbow 42, as shown. The plastic tubing 48 is connected at its other end to a source of a vacuum, vacuum pump 56 in this example. Note in this example that a control valve 58 is positioned between the separator tank 30 and the vacuum pump 56 to temporarily relieve the vacuum on the system to allow condoms 2 to be dumped from the separator tank 30 via the flapper valve 36. Also note that in this example, the randomizer vessels 14 are vertically mounted on a platform 50, with each of the vessels 14 having their lower portion protruding from a circular hole in the platform 50, as shown in the partial cross-sectional view thereof. Vertical rods 52 have clamping rings 54 secured to each rod 52, and secured around the associated randomizer vessel 14 at upper and lower portions thereof, respectively, as shown.

In operating the unrolling apparatus of FIG. 7, condoms 2 are fed into an input end of unroller tube 10, and travel down the unroller tube 10 as previously described, with the rolled portion 4 of each condom 2 being either inside, or outside the condom 2. The airflow within the unroller tube 10 will cause each condom 2 to travel with its central longitudinal axis substantially aligned with the longitudinal axis of the unroller tube 10. As previously explained, unrolling of condoms 2 with their rolled portion 4 on the outside is accomplished by inflation of the condoms 2, and frictional forces imposed by the inside walls of the tube 10 against the rolled portions 4 thereof. There is approximately a 50—50 chance of having a condom 2 enter the tube 10 with the rolled portion 4 right side out to permit unrolling of the condom 2 as it passes through the tube 10, as previously described. With the present invention, each randomizer vessel 14 increases the probability of properly orienting the condom 2 for passage to the next feed tube or unroller tube for unrolling. Through the use of just one randomizer vessel 14, 60% to 80% of the condoms 2 will be unrolled. Through use of two randomizer vessels 14, approximately 70% to 90% of the condoms 2 will be unrolled, and if three randomizer vessels are used 80% to 100% of the condoms 2 will be unrolled that are passed through the unroller system. In the present apparatus, by using a vacuum of six to ten inches of mercury, the condom obtains a velocity within the unroller tubes 10, 10A, 10B, and 10C of over 200 miles per hour. Note that the inside diameter of each of the unroller tubes 10, 10A, 10B, and 10C, can be slightly larger, equal to, or smaller than the outside diameter of the device being unrolled.

Condoms 2 passing from unroller tube 10 into the first randomizer vessel 14 will tumble about within the interior volume of the vessel 14, whereby those of condoms 2 that are unrolled will remain unrolled, and those that were not unrolled may be reoriented to pass into the next unroller tube 10A with the rolled portion 4 on the outside, as desired. Condoms 2 passing through the tubing 10A, are transferred into the second randomizer vessel 14, where the process is repeated, and then passed therefrom via unroller tube 10B into the third randomizer vessel 14, for again repeating the randomizing process, for final passage into unroller tube 10C to the separator tank 30. Because the condoms 2, in passing from the unroller tube 10C into the separator tank 30 are passing from a relatively small cross-section tubing into the large cross-section separator tank 30, the high velocity airflow within the tubing 10C is reduced to a low velocity airflow as the air enters into the large cross-section separator tank 30. This causes the condoms 2 which are heavier than the air to drop to the bottom of the separator tank 30, rather than being sucked up into the vacuum line 48. However, to prevent any random condoms 2 from entering into the vacuum line 48, screening material 46 is placed over the opening of the elbow tubing 42 within the separator tank 30. Note further that after each batch of condoms 2 pass through the apparatus for unrolling, the vacuum in vacuum line 48 is turned off via vacuum control valve 58 permitting the condoms 2 to fall from the separator tank 30 into a bin placed beneath the flapper valve 36 (the bin is not shown for purposes of simplicity).

Figure 8:
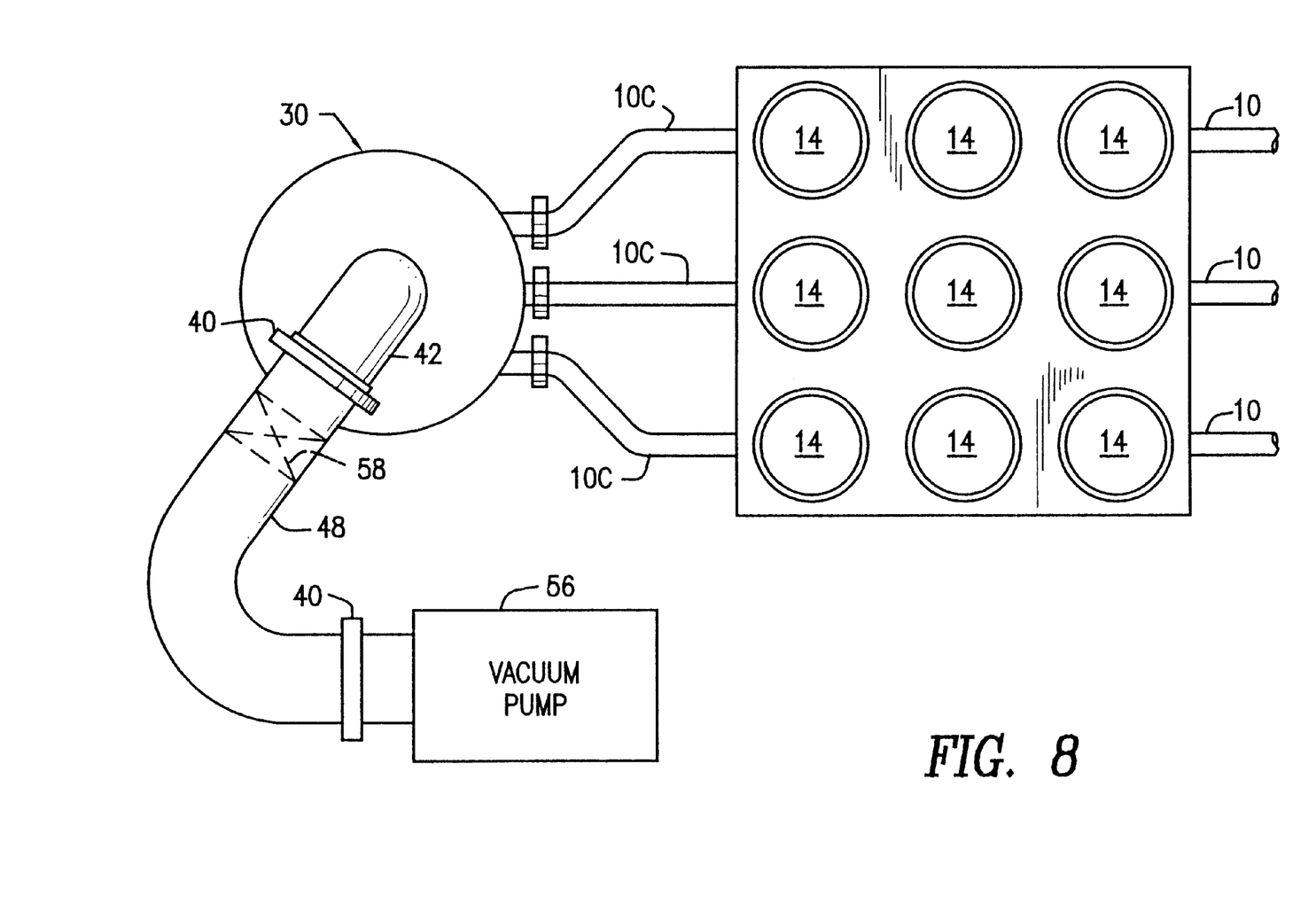
FIG. 8 shows a top view of a prophylactic product unrolling system of another embodiment of the invention using three banks of vacuum vessels, with each bank including three such vacuum vessels, for increasing the number of prophylactic devices capable of being unrolled in a given period of time through use of the apparatus.
Figure 9:
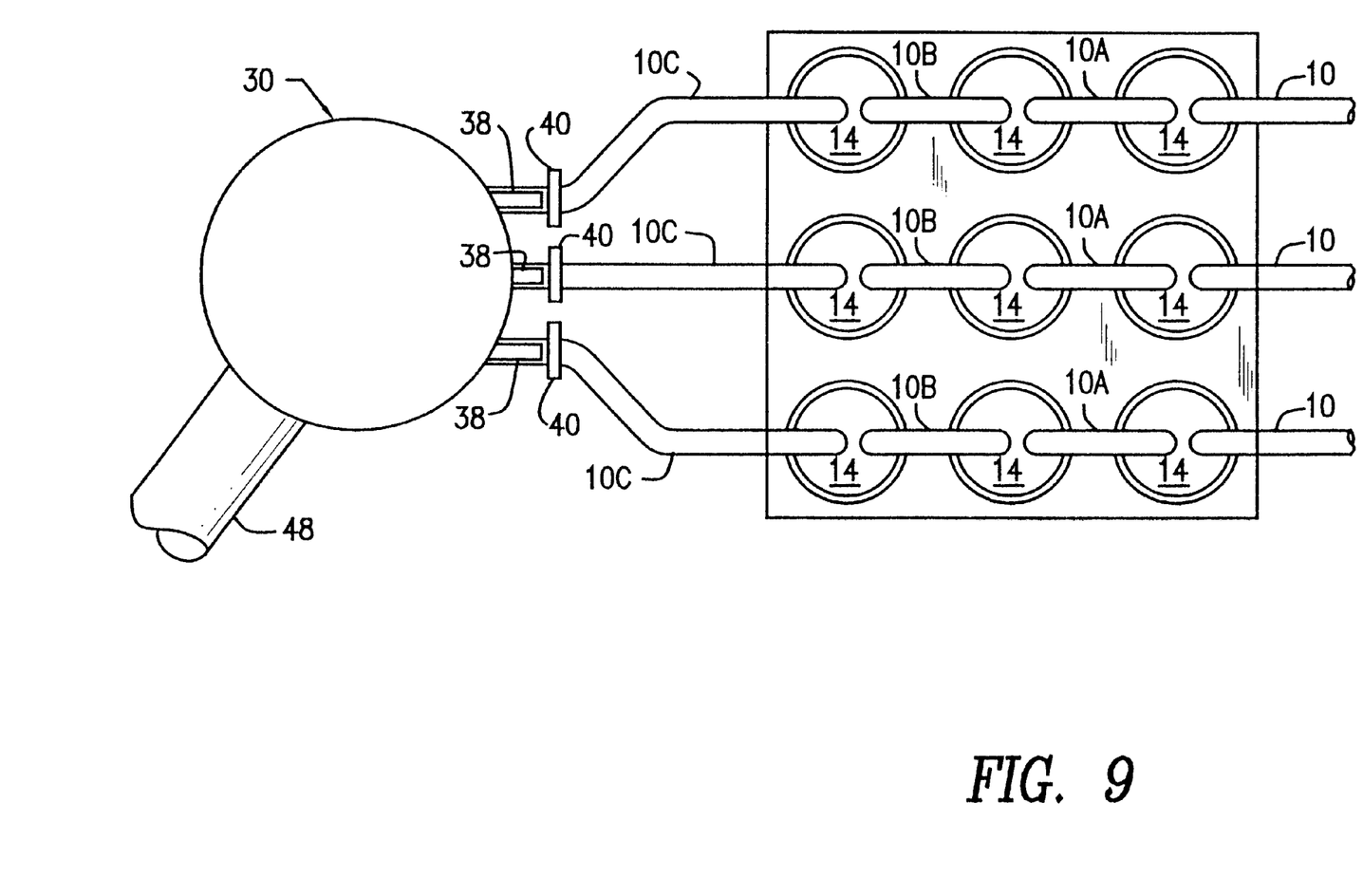
FIG. 9 shows a bottom view of the embodiment of the invention of FIG. 8.

To increase the number of condoms being unrolled in a given batch, the inventors developed an improved prototype system using three banks of the apparatus of FIG. 7, as shown in FIGS. 8 and 9. In FIG. 8, a top view of the improved apparatus is shown, and in FIG. 9 a bottom view is shown. Additional banks can be added beyond the three banks shown, up to a practical limit.

Although various embodiments of the invention have been shown and described herein, they are not meant to be limiting. Those of skill in the art may recognize certain modifications to these embodiments, which modifications are meant to be covered by the spirit and scope of the appended claims.

What is claimed is:

1. An apparatus for unrolling rolled-up prophylactic devices, comprising:

a plurality of unroller tubes, each having an input end and an output end through which spaced apart ones of said rolled-up prophylactic devices are passed for unrolling the ones of said devices that have their rolled-up portion located on the outside; and at least one randomizer means connected between output and input ends of a pair of said plurality of unroller tubes, respectively, for reorienting a portion of unrolled ones of said devices passing through said randomizer means to move the rolled-up portion of each said device from the inside to the outside thereof, before passage through another one of said plurality of unroller tubes.

2. The apparatus of claim 1, wherein said plurality of unroller tubes have inside diameters that are either slightly larger than, the same as, or smaller than, the outside diameter of said rolled-up prophylactic devices, respectively.

3. The apparatus of claim 2, further including:
a separator tank having an input port connected to the output end of the last one of said plurality of unroller tubes, a vacuum port, and a product removal port located at the bottom of said tank; and
a source of vacuum connected to the vacuum port of said separator tank, for sucking said prophylactic devices through said apparatus.

4. The apparatus of claim 2, wherein each one of said plurality of unroller tubes consist of material having smooth interior walls with a low coefficient of friction.

5. The apparatus of claim 4, wherein each one of said plurality of unroller tubes have an inside diameter that is larger than the outside diameter of a rolled-up prophylactic device.

6. The apparatus of claim 1, further including:
a plurality of randomizer means connected in cascade between output and input ends of successive pairs of said plurality of unroller tubes, respectively, for reorientating a portion of unrolled ones of said devices passing through each one of said plurality of randomizer means, before passage through another one of said plurality of unroller tubes, respectively, the greater the number of said plurality of randomizer means, the greater the percentage of unrolled prophylactic devices obtained and exiting from the output end of the final one of said plurality of unroller tubes.

7. The apparatus of claim 6, wherein said plurality of randomizer means each include a vessel including:
an uppermost elongated housing with a closed top portion having an interior hollow volume, and a funnel-shaped lowermost portion having a central outlet hole;
an input tube having one end secured to a hole in an upper portion of said funnel-shaped portion of said vessel, the other end of said input tube being for connection to an output end of one of said plurality of unroller tubes of a pair thereof and input end of said one of said plurality of unroller tubes being connected for receiving said prophylactic devices; and
an output tube having one end connected to said central outlet hole of said main housing central outlet hole of said main housing, and another end for connection to an input end of another one of said plurality of unroller tubes of a pair thereof.

8. The apparatus of claim 7, wherein said vessel consists of glass material.

9. The apparatus of claim 6, wherein said plurality of randomizer means each include a vessel including:
an enclosed housing having an interior hollow volume and top and bottom portions;
an input tube having one end secured to an input hole in a portion of said housing, the other end of said input tube being for connection to an output end of one of said plurality of unroller tubes being connected for receiving said prophylactic devices; and
an output tube having one end connected to an outlet hole of said enclosed housing, and another end for connection to an input end of another one of said plurality of unroller tubes of a pair thereof.

10. The apparatus of claim 1, further including:
a separator tank having an input port connected to the output end of said another unroller tube, a vacuum port, and a product removal port located at the bottom of said tank; and
a source of vacuum connected to the vacuum port of said separator tank, said vacuum source providing a vacuum for sucking air at relatively high velocity into the input end of a first one of said plurality of unroller tubes for passing said prophylactic devices through said apparatus.

11. The apparatus of claim 1, wherein said randomizer means includes a vessel including:
an uppermost elongated main housing with a closed top portion having an interior hollow volume, and a funnel-shaped lowermost portion having a central outlet hole;
an input tube having one end secured to a hole in an upper portion of said funnel-shaped portion of said vessel, the other end of said input tube being for connection to an output end of said one of said plurality of unroller tubes for permitting prophylactic devices to pass into said housing; and
an output tube having one end connected to said central outlet hole of said main housing, and another end for connection to an input end of said another one of said plurality of unroller tubes.

12. The apparatus of claim 11, wherein said vessel consists of glass material.

13. The apparatus of claim 12, wherein said vessel consists of glass material.

14. The apparatus of claim 1, wherein said randomizer means includes a vessel including:
an enclosed main housing having an interior hollow volume, and top and bottom portions;
an input tube having one end secured to an input hole in a portion of said housing, the end of said input tube being for connection to an output end of said one of said plurality of unroller tubes for permitting prophylactic devices to pass into said housing; and
an output tube having one end connected to an outlet hole of said main housing, and another end for connection to an input end of said another one of said plurality of unroller tubes.

15. The apparatus of claim 14, wherein said vessel consist of glass material.

16. The apparatus of claim 1, wherein each one of said plurality of unroller tubes consist of material having smooth interior walls with a low coefficient of friction.

17. The apparatus of claim 16, wherein each one of said plurality of unroller tubes have an inside diameter that is fractionally larger than the outside diameter of a rolled-up prophylactic device.

18. A method for unrolling rolled-up prophylactic device comprising the steps of:
passing spaced apart ones of a plurality of rolled-up prophylactic devices through a first unroller tube having an inside diameter that is fractionally larger than the outside diameter of each of said rolled-up prophylactic devices;
passing unrolled and rolled-up ones of said plurality of prophylactic devices from said first unroller tube into a randomizer vessel, a portion of the remaining rolled-up ones of said plurality of prophylactic devices being reoriented while moving through said first randomizer vessel for placing the rolled-up portion of each on the outside of its associated prophylactic device; and
passing the unrolled ones, reoriented rolled-up ones, and remaining other rolled-up ones of said plurality of prophylactic devices from said first randomizer vessel into and through a second unroller tube, for unrolling the reoriented ones of the remaining rolled-up said plurality of prophylactic devices.

19. The method of claim 18, further including the step of:

applying a vacuum to an output end of said second unroller tube for sucking said plurality of prophylactic devices through said first and second unroller tubes and said randomizer vessel therebetween.

20. The method of claim 19, wherein said vacuum applying step includes the steps of:

connecting an input port of a separator tank to an output end of said second unroller tube;

connecting a vacuum source to a vacuum port of said separator tank; and turning on said vacuum source for initiating unrolling of a majority of said plurality of rolled-up prophylactic devices on a batch basis.

21. The method of claim 20, further including the step of:

turning off said vacuum source to release a flapper valve to drop away from an outlet of a product delivery port at the bottom of said separator tank; and removing processed ones of said plurality of prophylactic devices.

22. The method of claim 18, further including the steps of:

connecting a plurality of said randomizer vessels in cascade between pairs of said first and second unroller tubes; and passing said prophylactic devices through said cascaded randomizer vessels and unroller tubes, whereby the number of said plurality of randomizer vessels, and pairs of first and second unroller tubes is selected to insure substantially all of said prophylactic devices passed therethrough are unrolled.

23. The method of claim 22, further including the step of:

applying a vacuum to an output end of a last one of said second unroller tubes for sucking said plurality of prophylactic devices through said cascaded randomizer vessels and unroller tubes.

24. The method of claim 23, wherein said vacuum applying step includes the steps of:

connecting an input port of a separator tank to the output end of said last one of said second unroller tubes;

connecting a vacuum source to a vacuum port of said separator tank; and turning on said vacuum source for initiating unrolling of a majority of said plurality of rolled-up prophylactic devices on a batch basis.

25. The method of claim 24, further including the steps of:

turning off said vacuum source to release a flapper valve to drop away from an outlet of a product delivery port at the bottom of said separator tank; and removing processed ones of said plurality of prophylactic devices.

26. An apparatus for unrolling rolled-up prophylactic devices, comprising:

a first unroller tube having an inside diameter that is fractionally larger than the diameter of said rolled-up prophylactic devices, said first unroller tube having an input end for receiving said prophylactic devices, and an output end;

at least a first randomizer vessel having an input port connected to the output end of said first unroller tube for receiving said prophylactic devices therefrom, and an output port;

a second unroller tube having an input end connected to the output port of said first randomizer vessel, and an output end;

a separator tank having an input port proximate a top portion of said tank connected to said output end of said second unrolling tube, a vacuum port, and a product removal port located at the bottom of said tank;

a vacuum source having an input port; and a vacuum line connected between said vacuum port of said separator tank, and said input port of said vacuum source, wherein with said vacuum source energized a batch of prophylactic devices are individually fed into the input end of said first unroller tube, and sucked therethrough into said first randomizer vessel, a portion of said prophylactic devices having been unrolled in said first unroller tube, and a portion remaining rolled-up, whereby as said prophylactic devices move through said first randomizer vessel, a portion of the remaining rolled-up ones are randomly reoriented to have their rolled-up portion on the outside thereof to facilitate subsequent unrolling as they are sucked from said first randomizer vessel through said second unroller tube into said separator tank for removal from said product removal port.

* * * * *